(12) United States Patent
Holdsworth et al.

(10) Patent No.: US 11,402,515 B2
(45) Date of Patent: Aug. 2, 2022

(54) GAMMA PROBE AND MULTIMODAL INTRAOPERATIVE IMAGING SYSTEM

(71) Applicants: David W. Holdsworth, London (CA); Mohammad Ali Tavallaei, Scarborough (CA); John Matheson, London (CA); Asha Parekh, London (CA)

(72) Inventors: David W. Holdsworth, London (CA); Mohammad Ali Tavallaei, Scarborough (CA); John Matheson, London (CA); Asha Parekh, London (CA)

( * ) Notice: Subject to any disclaimer, the term of this patent is extended or adjusted under 35 U.S.C. 154(b) by 336 days.

(21) Appl. No.: 16/306,450

(22) PCT Filed: May 31, 2017

(86) PCT No.: PCT/CA2017/050662
§ 371 (c)(1),
(2) Date: Nov. 30, 2018

(87) PCT Pub. No.: WO2017/205978
PCT Pub. Date: Dec. 7, 2017

(65) Prior Publication Data
US 2019/0154845 A1 May 23, 2019

Related U.S. Application Data

(60) Provisional application No. 62/343,421, filed on May 31, 2016.

(51) Int. Cl.
*G01T 1/161* (2006.01)
*A61B 6/00* (2006.01)
(Continued)

(52) U.S. Cl.
CPC ............ *G01T 1/161* (2013.01); *A61B 6/4258* (2013.01); *A61B 6/4405* (2013.01);
(Continued)

(58) Field of Classification Search
CPC ....... G01T 1/161; G01T 1/1603; G21K 1/025; A61B 6/4405; A61B 6/4258;
(Continued)

(56) References Cited

U.S. PATENT DOCUMENTS 3,407,300 A * 10/1968 Hansen ................. G21K 1/025
378/149
3,997,793 A 12/1976 Rogers et al.
(Continued)

FOREIGN PATENT DOCUMENTS

GB 2530254 A * 3/2016 ............. A61B 90/30
WO 9523552 A1 9/1995
WO 2015173841 A2 11/2015

OTHER PUBLICATIONS

Jaszczak, R. J., Greer, K. L., & Coleman, R. E. . SPECT using a specially designed cone beam collimator. (1988) Journal of nuclear medicine, 29(8), 1398-1405. (Year: 1988).*
(Continued)

*Primary Examiner* — Jason M Ip
*Assistant Examiner* — Renee C Langhals
(74) *Attorney, Agent, or Firm* — Brunet & Co. Ltd.; Robert Brunet; Hans Koenig (57) ABSTRACT

An intraoperative imaging system combines a gamma probe and an ultrasound probe. The probes are linked to provide co-registration of gamma radiation detected by the gamma probe with an image acquired by the ultrasound probe. The gamma probe has a converging collimator made of a metal block having a plurality of channels therein, which converge from an output face toward an input face. Each channel extends between and opens out at the faces such that openings at the input face have smaller cross-sectional areas than openings at the output face so that each channel tapers inwardly from the output face to the input face. The collimator has an external focal point distant from the input face.

(Continued)

The system improves identification and localization of cancerous cells, facilitating more accurate biopsy data and more complete surgical resection. The gamma probe increases sensitivity, while maintaining spatial resolution, and increasing depth of view.

14 Claims, 10 Drawing Sheets

(51) Int. Cl.
- A61B 8/08 (2006.01)
- A61B 8/00 (2006.01)
- G01T 1/16 (2006.01)
- G21K 1/02 (2006.01)
- A61B 90/00 (2016.01)
- A61B 34/20 (2016.01)
- A61B 90/30 (2016.01)

(52) U.S. Cl.
CPC .......... *A61B 6/4417* (2013.01); *A61B 6/5235* (2013.01); *A61B 8/085* (2013.01); *A61B 8/4416* (2013.01); *A61B 8/5246* (2013.01); *G01T 1/1603* (2013.01); *G21K 1/025* (2013.01); *A61B 34/20* (2016.02); *A61B 2090/309* (2016.02); *A61B 2090/3612* (2016.02); *A61B 2090/378* (2016.02)

(58) Field of Classification Search
CPC ..... A61B 6/4417; A61B 6/5235; A61B 8/085; A61B 8/4416; A61B 8/5246; A61B 34/20; A61B 2090/3612; A61B 2090/309; A61B 2090/378
USPC ........................................................ 600/436
See application file for complete search history.

(56) References Cited

U.S. PATENT DOCUMENTS

| | | |
|---|---|---|
| 6,021,341 A | 2/2000 | Scibilia et al. |
| 6,212,423 B1 | 4/2001 | Krakovitz |
| 6,484,050 B1 | 11/2002 | Carroll et al. |
| 6,495,834 B1 | 12/2002 | Corvo et al. |
| 6,510,336 B1 | 1/2003 | Daghighian et al. |
| 7,847,274 B2 | 12/2010 | Kornblau et al. |
| 8,521,253 B2 | 8/2013 | Melman |
| 8,606,349 B2 | 12/2013 | Rousso et al. |
| 8,831,708 B2 | 9/2014 | Paladini |
| 9,271,686 B2 | 3/2016 | Majewski et al. |
| 9,345,441 B2 | 5/2016 | Wendler |
| 2002/0168317 A1 | 11/2002 | Daighighian et al. |
| 2003/0209677 A1 | 11/2003 | Kumakhov |
| 2004/0075058 A1 | 4/2004 | Blevis et al. |
| 2008/0042067 A1 | 2/2008 | Rousso et al. |
| 2008/0128626 A1* | 6/2008 | Rousso ................. G01T 1/2985 250/362 |
| 2008/0161632 A1 | 7/2008 | Rozenfeld et al. |
| 2009/0078875 A1 | 3/2009 | Rousso et al. |
| 2009/0112086 A1 | 4/2009 | Melman |
| 2009/0127459 A1 | 5/2009 | Neustadter et al. |
| 2010/0025587 A1* | 2/2010 | Benlloch Baviera .. A61B 90/36 250/362 |
| 2010/0245354 A1 | 9/2010 | Rousso et al. |
| 2010/0266171 A1 | 10/2010 | Wendler et al. |
| 2011/0198510 A1 | 8/2011 | Neustadter et al. |
| 2013/0172739 A1* | 7/2013 | Paladini ................ A61B 6/5247 600/436 |
| 2013/0237811 A1 | 9/2013 | Mihailescu et al. |
| 2014/0276032 A1 | 9/2014 | Majewski et al. |
| 2015/0213912 A1 | 7/2015 | Sakai et al. |
| 2015/0262721 A1 | 9/2015 | Suzuki et al. |

OTHER PUBLICATIONS

International Search Report and Written Opinion dated Sep. 7, 2017 on International Patent Application PCT/CA2017/050662.

* cited by examiner

Fig. 10B

GAMMA PROBE AND MULTIMODAL INTRAOPERATIVE IMAGING SYSTEM

CROSS-REFERENCE TO RELATED APPLICATIONS

This application is a national phase entry of International Patent Application PCT/CA2017/050662 filed May 31, 2017 and claims the benefit of U.S. Provisional Patent Application Ser. No. 62/343,421 filed May 31, 2016, the entire contents of both of which are herein incorporated by reference.

FIELD

This application relates to a gamma probe and a hybrid device comprising the gamma probe for performing intra-operative hybrid imaging. In particular, ultrasound imaging and nuclear medicine imaging are combined to provide an optimized multimodality system.

BACKGROUND

Breast cancer is the second leading cause of death in North American women; over 40,000 women are expected to die from breast cancer in North America this year. Most women with breast cancer undergo surgery, either to remove a breast tumor or to check the lymph nodes for cancer spread.

Image guidance during surgery is provided by intra-operative ultrasound or, in some cases, gamma detectors and cameras. The additional information provided by intra-operative imaging can ensure that the breast tumor is entirely removed, leaving a negative margin, and that cancer has not spread to nearby lymph nodes. Unfortunately, with existing techniques, there is still a repeat surgery rate of 25% for breast cancer patients.

Recent developments in radiochemistry and nuclear imaging have resulted in the possibility of intra-operative gamma imaging of radiolabeled tissue. In these procedures, radiolabeled compounds with high affinity for tumor cells can enhance the intraoperative detection of the tumor margin, using either non-imaging probes or small-field gamma cameras. However, current gamma probes provide poor spatial resolution, and scintigraphic cameras are too slow for real time imaging.

Ultrasound provides relatively high resolution images of tissue boundaries, facilitating localization of lymph nodes and tumor margins, and as previously mentioned, gamma detectors can identify "hot" tissues, which have been radioactively labeled for biopsy or resection.

Hybrid solutions that take advantage of the information provided by the gamma detectors combined with other imaging modalities, such as ultrasound, have had minimal traction in the clinic due to limitations, such as low frame rate, low sensitivity, low specificity, and limited anatomical information.

Thus, there still exists a need to improve sensitivity and specificity of intra-operative systems used for surgical resection and biopsy of tumors, in order to improve the identification and localization of cancerous cells and facilitate complete tumor resection.

SUMMARY

A multimodality medical imaging device is provided comprising a gamma probe and an ultrasound probe. The gamma probe may comprise a collimator and one or more gamma detectors.

In one aspect, there is provided an intraoperative imaging system comprising a gamma probe configured to detect gamma radiation emitted from a radiolabeled tissue and an ultrasound probe configured to acquire an ultrasound image of the radiolabeled tissue, the gamma probe and ultrasound probe linked to provide co-registration of the gamma radiation with the ultrasound image, the gamma probe comprising a converging collimator for gamma rays, the collimator comprising: a metal block having a gamma ray input face and a gamma ray output face; a plurality of channels in the metal block converging from the output face toward the input face, each channel extending between the input face and the output face, each channel having a first opening at the input face and a second opening at the output face, wherein the first opening has a smaller cross-sectional area than a cross-sectional area of the second opening and each channel tapers inwardly from the output face to the input face; and, a focal point outside the collimator and distant from the input face.

In another aspect, there is provided a converging collimator for gamma rays, the collimator comprising: a metal block having a gamma ray input face and a gamma ray output face; a plurality of channels in the metal block converging from the output face toward the input face, each channel extending between the input face and the output face, each channel having a first opening at the input face and a second opening at the output face, wherein the first opening has a smaller cross-sectional area than a cross-sectional area of the second opening and each channel tapers inwardly from the output face to the input face; and, a focal point outside the collimator and distant from the input face.

In another aspect, there is provided a gamma probe comprising the collimator as described above and a gamma radiation detector situated to receive gamma rays from the output face of the collimator.

In another aspect, there is provided a method of imaging a radiolabeled tissue in a body of a patient in real-time, the method comprising: acquiring an ultrasound image and a corresponding gamma ray count at a location in the body with an intraoperative imaging system as described above; and, displaying in real-time the ultrasound image with the corresponding gamma ray counts co-registered thereon to determine whether the radiolabeled tissue is at the location.

The collimator may be a converging collimator. The collimator may have one focal point or multiple focal points. Where the collimator has a plurality of sections giving rise to multiple focal points, multiple gamma detectors may be used to detect gamma radiation received from each section of the collimator corresponding to a specific focal point. The collimator may have one, two, three, four or more sections, any two sections having the same or different focal points. In one example, the collimator may have two sections that have adjacent focal points in the x-y plane. Detected gamma values from each of the focal points may be used to identify direction towards a source of radiation (hot spot) through an audio or visual feedback to a user. The collimator may provide a matrix coverage of a plane of interest. One, two, three, four or more gamma detectors may be provided in the gamma probe. The gamma probe preferably has a spatial resolution in an x-y plane of 6 mm or less. One or two or more of the gamma detectors may be used to obtain a stereo measurement of gamma radiation values coming from the same focal point and to allow for an accurate estimation of a depth of a source of the gamma radiation.

The ultrasound probe may be, for example, a 2D ultrasound imaging transducer or a 3D ultrasound imaging system utilizing multiple arrays of ultrasound transducers.

The gamma probe may be tracked spatially. The gamma probe and ultrasound probe may be mechanically linked such that they can be moved and tracked relative to each other with confined kinematics. Alternatively, the gamma probe and ultrasound probe may not be mechanically linked and the two imaging modalities tracked independently using a tracking system, such as an optical, a mechanical or an electromagnetic tracking system.

The ultrasound probe may be tracked spatially and be swept across tissue while images are recorded with a tag of positions from which the images were acquired. The acquired images may be used to reconstruct a 3D image of the tissue. The tracked position of the gamma probe may be registered with preoperative 3D volumetric images obtained from the patient (e.g. computer tomography (CT) images or magnetic resonance images (MRI)). Anatomical landmarks on a patient may be pointed to with the gamma probe as the gamma probe is tracked. The points may be identified on preoperative images and used to register the gamma probe position relative to the 3D volumetric images. Relative positions of the ultrasound probe and the gamma probe may be measured using known kinematics of the assembly and by measurement of joint positions and angles using sensors. Relative spatial tracking information of the two imaging modalities may be used for co-registration of the acquired images. The relative position of the two imaging modalities may be adjusted manually or by using an actuator. The relative position of the two imaging modalities may be adjusted so that the focal point of the gamma probe is maintained within an imaging field of the ultrasound probe.

Gamma radiation detected values and ultrasound images may be represented visually to the user on an output device. An estimate of spatial positioning of the source of gamma radiation, alongside a graphical representation of the amount of activity, may be overlaid on acquired ultrasound images and presented in real-time.

A third imaging modality may be included in the multi-modality medical imaging device. The third imaging modality may be a visible light modality. The visible light imaging modality may comprise an optical light source used in conjunction with a confocal convergent collimator to project visible light onto the patient body providing visual feedback to provide an estimate for the position of the focal point relative a skin surface of the body. An optical imaging camera may be mounted on the gamma probe to measure size of the projected visible light and to calculate an estimate for relative position of the focal point to the skin surface.

A real-time gamma probe is provided that can detect gamma radiation from a small region of interest located several cm away from a face of the probe through the use of a highly-focused collimator. The gamma probe may be utilized in radio-guided surgery, for example in ensuring adequate margins during tumor resection and in identifying labeled lymph nodes during sentinel node biopsy. The gamma probe improves identification and localization of cancerous cells, facilitating more accurate biopsy data and more complete surgical resection. The design of the gamma probe increases sensitivity, while maintaining spatial resolution, and increasing depth of view. The highly-focused collimator can collect a significant fraction (e.g. over 0.5%) of all gamma photons emitted by the gamma ray source, ensuring that detected count rates are high enough for real-time feedback to the operator. For example, labeled tissue in intraoperative applications generally exhibit activity an order of magnitude higher than the sensitivity of the present gamma probe.

Further, the highly-focused collimator design may have a remote focal zone, designed to be located at a pre-defined distance from the collimator face, while retaining x-y spatial resolution. Therefore, the gamma probe can be incorporated with other imaging modalities, for example ultrasound (e.g. B-mode ultrasound), to provide co-registered functional and anatomical information during one hand-held scan. By tracking the relative position of the gamma probe to the position of the patient and another imaging modality, e.g. ultrasound, the radioactivity can be reported within a co-registered region of interest. This co-registered region can be displayed in real time, with information from both the gamma probe and the second imaging modality used, e.g. ultrasound, or pre-acquired geometric computer tomography (CT).

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
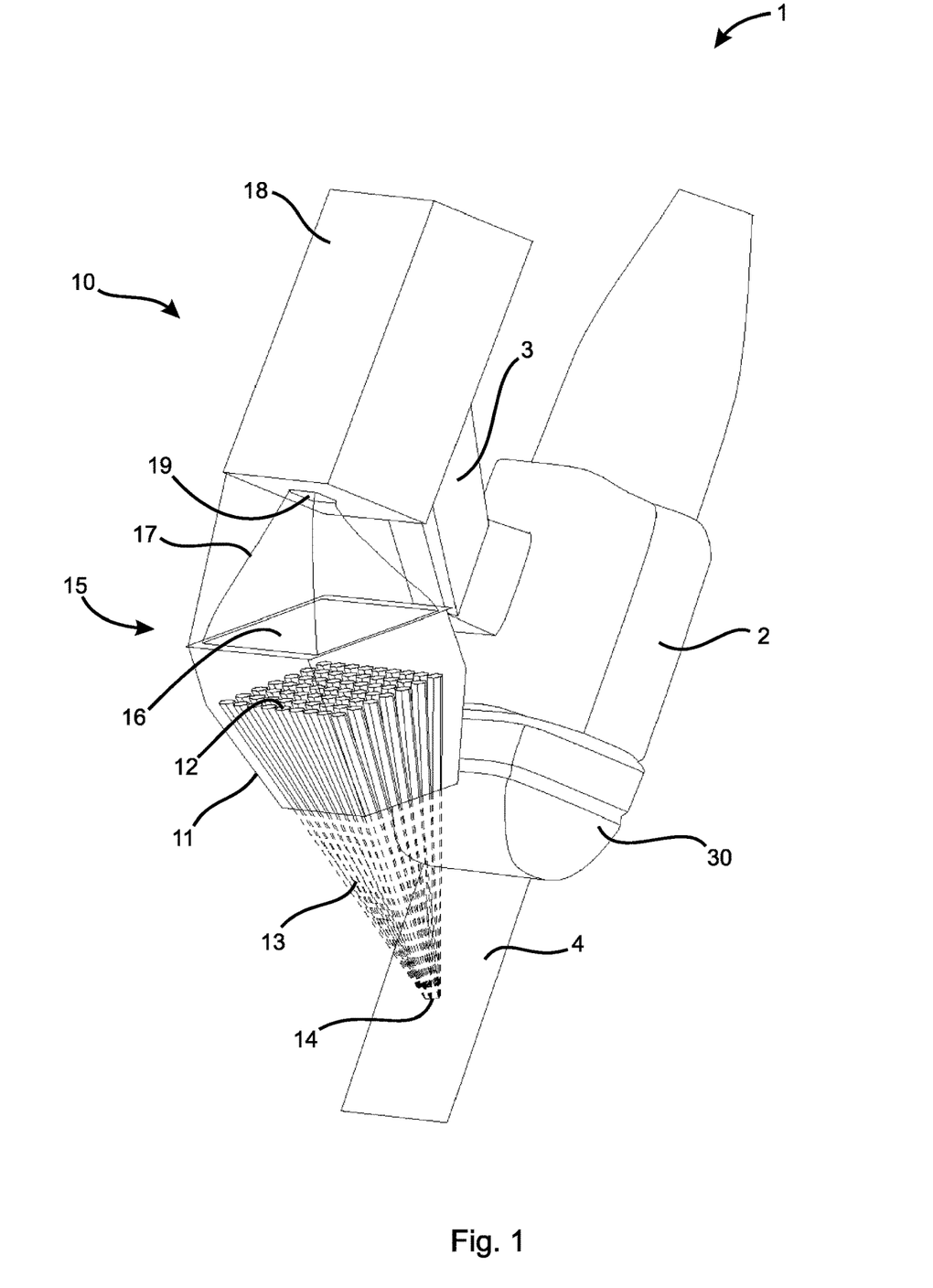
FIG. 1 depicts a schematic drawing of one embodiment of a handheld combined gamma and ultrasound intraoperative imaging system, the intraoperative imaging system comprising a gamma probe in accordance with the present invention.

FIG. 1 depicts a schematic drawing of one embodiment of a handheld combined gamma and ultrasound intraoperative imaging system 1. The intraoperative imaging system 1 may comprise a handheld gamma probe 10 mechanically linked to a handheld ultrasound probe 30, for example a Philips L 12-5 ultrasound probe, through a mounting bracket 2. The mounting bracket 2 may comprise a translation stage 3 that provides for vertical co-localization of gamma and ultrasound imaging. The gamma probe 10 may be mounted on the translation stage 3, the translation stage moveable to permit vertical translation (i.e. translation along a z-axis) of the gamma probe 10 relative to a position of the ultrasound probe 30 and relative to a horizontal plane (i.e. an x-y plane).

The gamma probe 10 may comprise a highly sensitive convergent collimator 11 coupled to a large area gamma radiation detector 15 to provide real-time "spot" measurements of radiation intensity within specific regions of interest. The collimator 11 may comprise a plurality of tapered channels 12 (only one labeled) configured to provide for gamma ray paths 13 through the collimator 11 that converge at a specified focal point 14 in an ultrasound image acquisition plane 4 below the gamma probe 10. Only gamma rays originating from the focal point 14 are able to pass through the channels 12 into the radiation detector 15 to be detected therein. The focal point is typically several millimeters in diameter.

The large area radiation detector 15 of the gamma probe 10 may comprise a scintillator 16 disposed above the collimator 11, a light guide 17 disposed above the scintillator 16 and a photomultiplier module 18 disposed above the light guide 17. The scintillator 16 may be configured to receive gamma rays from the collimator 11, the scintillator 16 emitting visible light upon interaction with the gamma rays. The scintillator may comprise a high-Z material, for example inorganic crystals such as BaF, NaI, undoped CsI, CsI doped with Na and the like. Scintillators are generally known in the art, and the choice of scintillator depends to some extent on the radioisotope being detected and/or the photomultiplier module. The energy selectivity of the scintillator should match the energy of the gamma rays emitted by the radioisotope. For example, the scintillator 16 may comprise a 10-mm thick crystal of CsI(Na) and the photomultiplier module may be a compact Hamamatsu H9306-01 photomultiplier module. The light guide 17 may be configured to collect and guide gamma rays from the scintillator 16 to an input window 19 of the photomultiplier module 18. The light guide may comprise a tapered structure comprising a visible light reflective material (e.g. a plastic). For example, a tapered polished acrylic (e.g. polymethylmethacrylate (PMMA)) light guide 17 may be utilized. The photomultiplier module 18 detects the visible light entering through the input window 19 and provides an electrical signal to an output device providing an indication of the intensity of gamma radiation being detected by the gamma probe 10.

To enhance sensitivity and resolution of the gamma probe 10 over a small field of view (FOV), the channels 12 are configured so that longitudinal axes of the channels 12 converge below the gamma probe 10. Importantly, each of the channels 12 is also tapered from top to bottom such that a cross-sectional area of each of the channels 12 is larger at a top of the channels 12 than at a bottom of the channels 12. Such tapering provides for a significant enhancement in detection efficiency over a smaller field of view. The collimator 11 may comprise a block of metal, preferably a dense metal (e.g. stainless steel, cobalt-chrome alloy, tungsten, alloys thereof or the like), having the converging tapered channels 12 formed therein. The collimator 11 in FIG. 1 is illustrated having 112 tapered hexagonal channels 12 fabricated within a 20-mm thick metal block.

In one example, the gamma probe 10 may provide about 54% collimator transmission efficiency, about 90% scintillator quantum efficiency, about 1.9% counting efficiency and 42,000 counts per minute (CPM) $\mu Ci^{-1}$.

The collimator may comprise any number of channels of any suitable cross-sectional shape, for example hexagonal, circular or rectangular. More channels increase sensitivity at the expense of compactness. Hexagonal channels provide significantly better spatial resolution than cylindrical channels or rectangular channels. Tapered channels provide greater sensitivity and higher detection efficiency by providing higher throughput of gamma rays to the radiation detector. Each of the channels preferably has a taper angle in a range of about 0.8° to about 6°, with respect to the longitudinal axis of the channel. The taper angle is more preferably in a range of about 1° to about 3°. The desired taper angle depends to some extent on the desired focal point of the channels.

Tapering of each channel in a cluster of channels in a single metal block has hitherto been impossible to achieve. However, it is now possible through the use of additive manufacturing (e.g. 3D metal printing) to construct collimator assemblies having any number of channels with longitudinal axes oriented in any configuration, and having each channel tapered at a desired angle. Such control over collimator design through additive manufacturing permits construction of a wide variety of collimators for a variety of different applications.

Figure 2A:
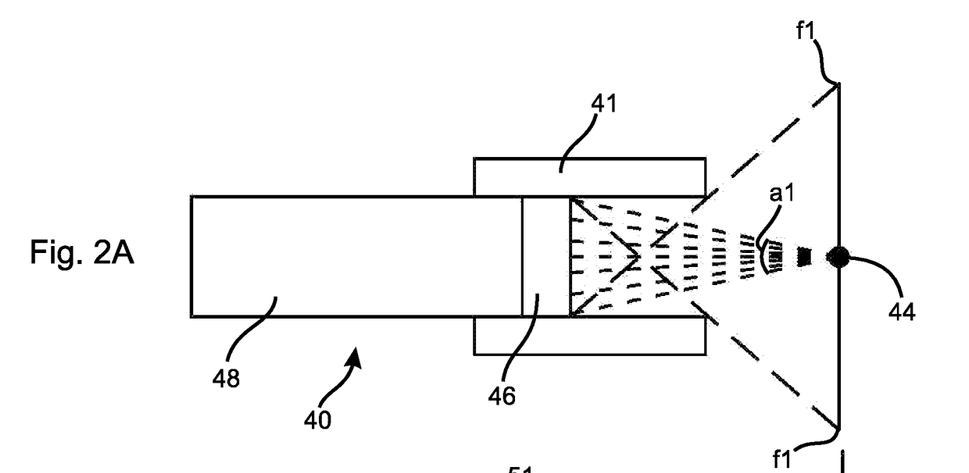
FIG. 2A depicts a schematic diagram of gamma ray paths in a conventional intraoperative gamma probe used in intraoperative imaging systems of the prior art.
Figure 2B:
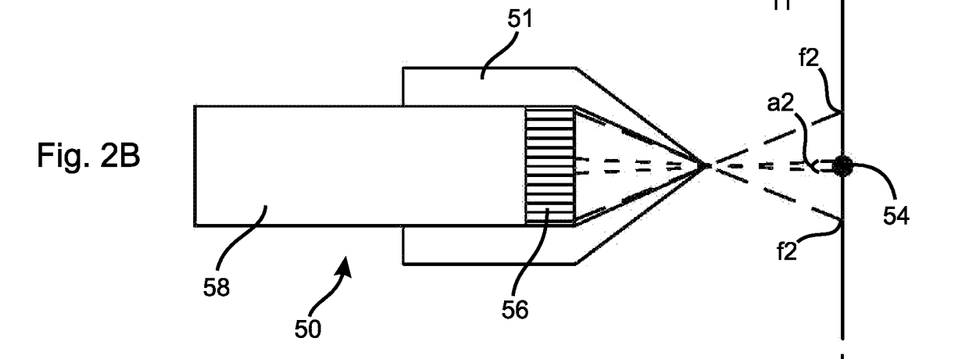
FIG. 2B depicts a schematic diagram of gamma ray paths in an intraoperative gamma camera used in intraoperative imaging systems of the prior art.
Figure 2C:
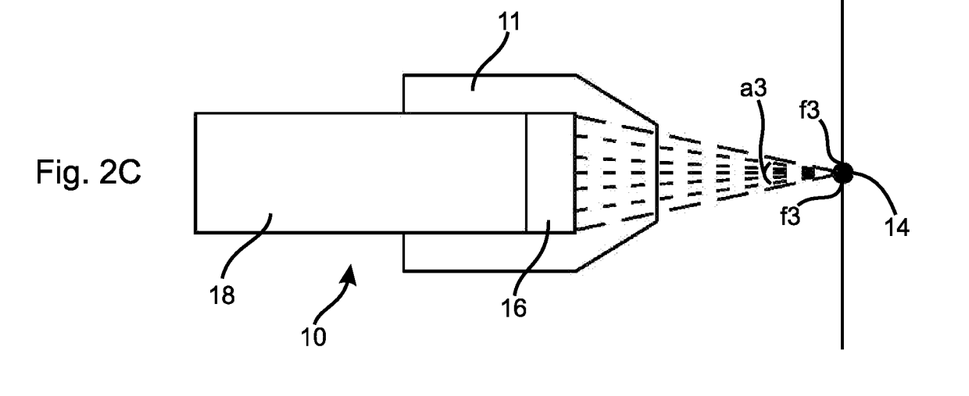
FIG. 2C depicts a schematic diagram of gamma ray paths in a gamma probe used in the intraoperative imaging system of FIG. 1.

FIG. 2A, FIG. 2B and FIG. 2C depict a comparison of intraoperative gamma imaging systems. A conventional gamma probe 40 (FIG. 2A) has a scintillating crystal 46 (a single detector) in a simple open-faced collimator 41, the scintillating crystal 46 coupled to a photomultiplier tube 48. The conventional gamma probe 40 can be used for real-time imaging, and has a large acceptance angle a1 for gamma rays emanating from a node 44 leading to good sensitivity when held directly against tissue. However, the conventional gamma probe 40 has an indiscriminate field of view f1 leading to an undesirably large field of view and poor spatial resolution, especially at a distance from the tissue. A conventional gamma camera 50 (FIG. 2B) has a matrix array detection system 56 in a pinhole collimator 51, the matrix array detection system 56 further comprising a position sensitive detector 58. The conventional gamma camera 50 has an acceptably low field of view f2 leading to good spatial resolution. However, the conventional gamma camera 50 has a small acceptance angle a2 for gamma rays emanating from a node 54, the collimator 51 excluding a majority of the gamma ray photons leading to poor sensitivity. Further, the matrix array detection system 56 leads to long image acquisition times, which is unacceptable for real-time applications. The presently disclosed gamma probe 10 (FIG. 2C) has the scintillating crystal 16 (a single detector) in the highly convergent collimator 11, the scintillating crystal 46 coupled to the photomultiplier module 18. The gamma probe 10 has a large acceptance angle a3 for gamma rays emanating from a focal node 14 leading to high sensitivity, and has a small field of view f3 leading to very good spatial resolution. The gamma probe 10 can be used for real-time spot imaging, and the collimator 11 is not required to be held directly against tissue. The gamma probe 10 can be effective in real-time scanning during surgery or biopsy, allowing a surgeon to interrogate specific tissue locations to detect the presence of radioactive tracers.

Figure 3A:
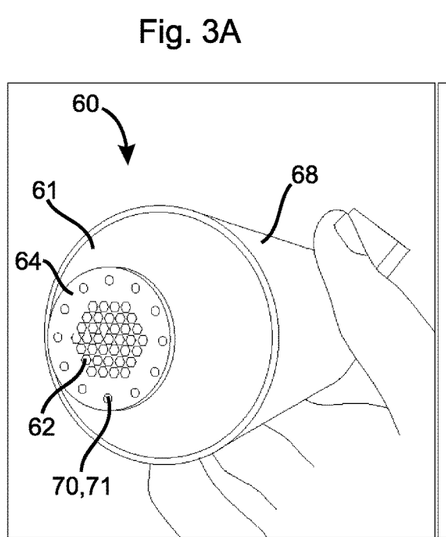
FIG. 3A depicts an embodiment of a handheld gamma probe in accordance with the present invention.
Figure 3B:
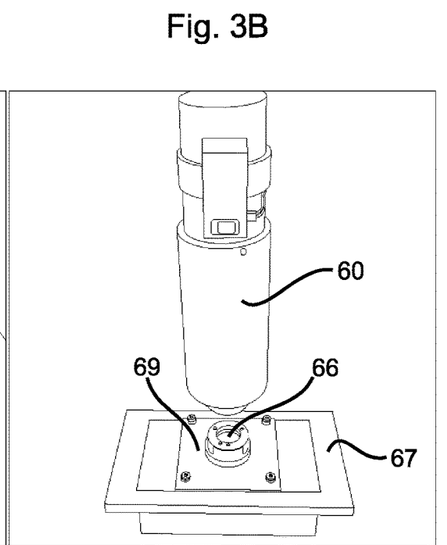
FIG. 3B depicts the gamma probe of FIG. 3A mounted over a motorized stage during tests of spatial resolution and sensitivity.
Figure 3C:
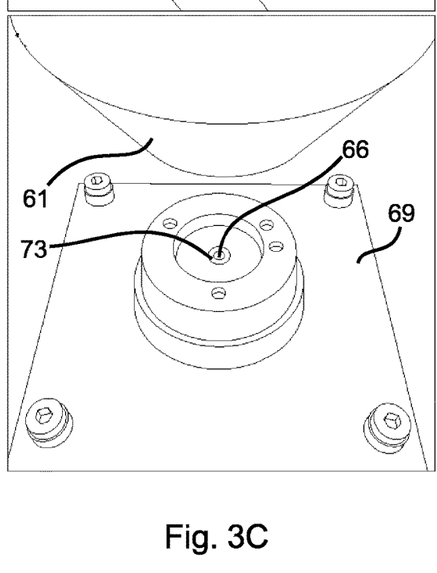
FIG. 3C depicts a magnified view of the gamma probe of FIG. 3A over a gamma source mounted on the motorized stage depicted in FIG. 3B showing visible light co-localization of the gamma source.
Figure 3D:
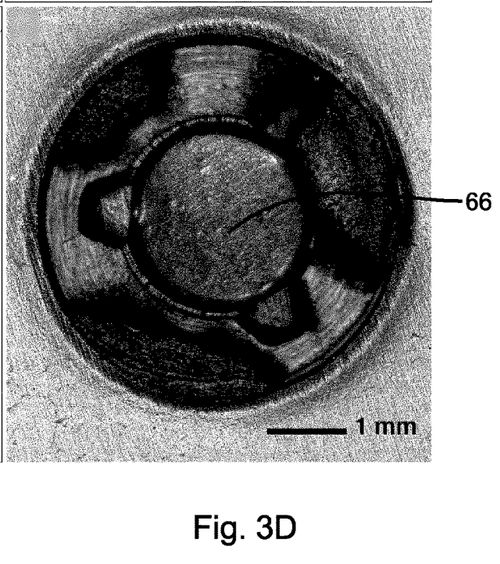
FIG. 3D depicts a magnified view of the gamma source depicted in FIG. 3C showing a 2-mm diameter active area.

FIG. 3A depicts an embodiment of a handheld gamma probe 60 of the present invention that may be utilized in a handheld combined gamma and ultrasound intraoperative imaging system. FIG. 3B and FIG. 3C depict the gamma probe 60 set up for testing spatial resolution and count-rate sensitivity. FIG. 3C shows a spot of visible light 73 from an optical alignment system mounted on the collimator 61 colocalized on the gamma ray source 66. In FIG. 3A, the gamma probe 60 is shown mounted over a motorized stage 67 on which a 0.9 µCi $^{241}$Am (Americium dioxide) gamma ray source 66 having an active area diameter of about 2 mm is mounted. FIG. 3D is a magnified view of the gamma ray source 66.

The gamma probe 60 (FIG. 3A) comprises a conventional crystal-based gamma detector 68 and a highly convergent focused collimator 61 in accordance with present invention attached to the conventional gamma detector 68. The conventional crystal-based gamma detector (Model 44-2, Ludlum) comprises a 2.5 cm diameter NaI crystal (2.5 cm thick) coupled to a photomultiplier tube. High-voltage is provided by a hand-held rate-meter (Model 3, Ludlum). To reduce the background count rate, the crystal/PMT assembly is enclosed within an additional 3 mm of lead sheet. A dedicated pulse-counting circuit based on a programmable microcontroller (Atmel ATMEGA2560) allows results from the analog rate-meter to be quantified and recorded for subsequent analysis.

Figure 4A:
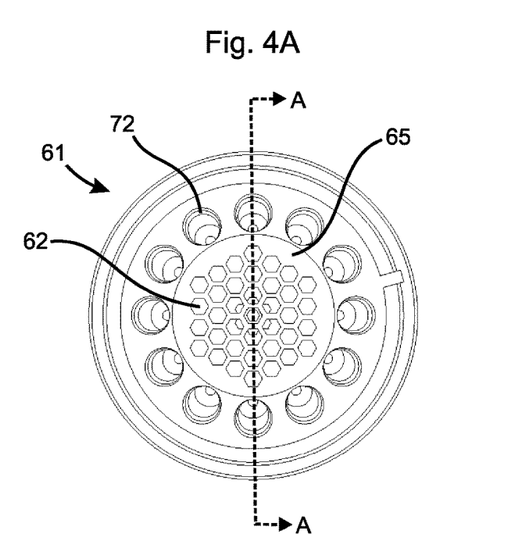
FIG. 4A depicts a schematic diagram of a top face of a collimator in the gamma probe of FIG. 3A.
Figure 4B:
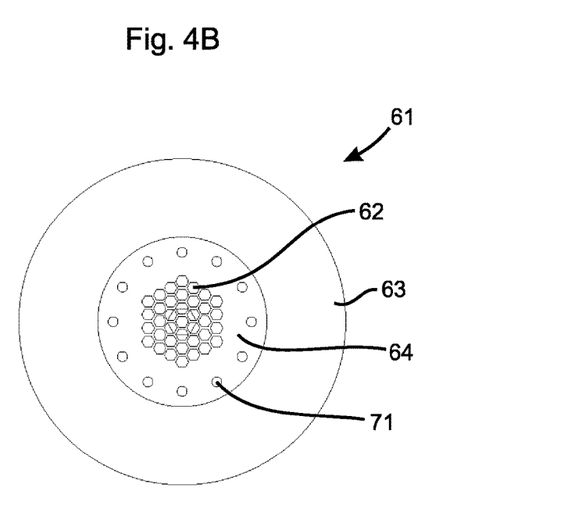
FIG. 4B depicts a schematic diagram of a bottom face of the collimator of FIG. 4A.
Figure 4C:
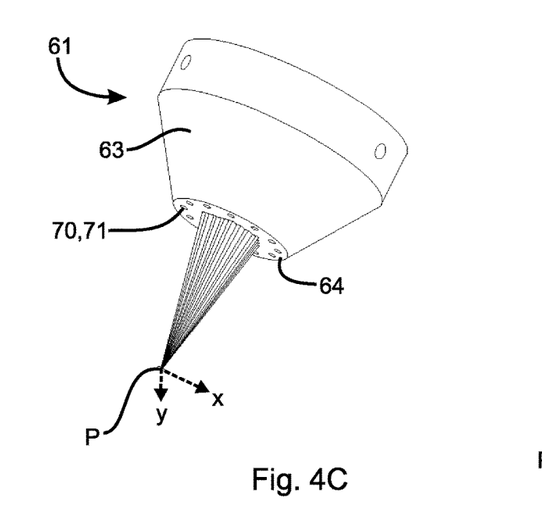
FIG. 4C is a schematic diagram illustrating that gamma ray paths from 37 tapered hexagonal channels in the collimator of FIG. 4A converge at a focal spot (one point) 35 mm below the bottom face of the collimator.
Figure 4D:
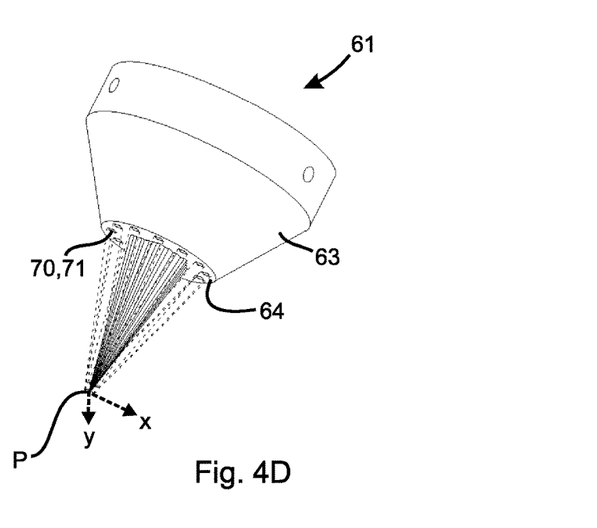
FIG. 4D is a schematic diagram illustrating that visible light from high intensity light emitting diodes (LEDs) mounted around a periphery of the bottom face of the collimator of FIG. 4C are co-aligned with the collimator focal spot providing visual localization.
Figure 5:
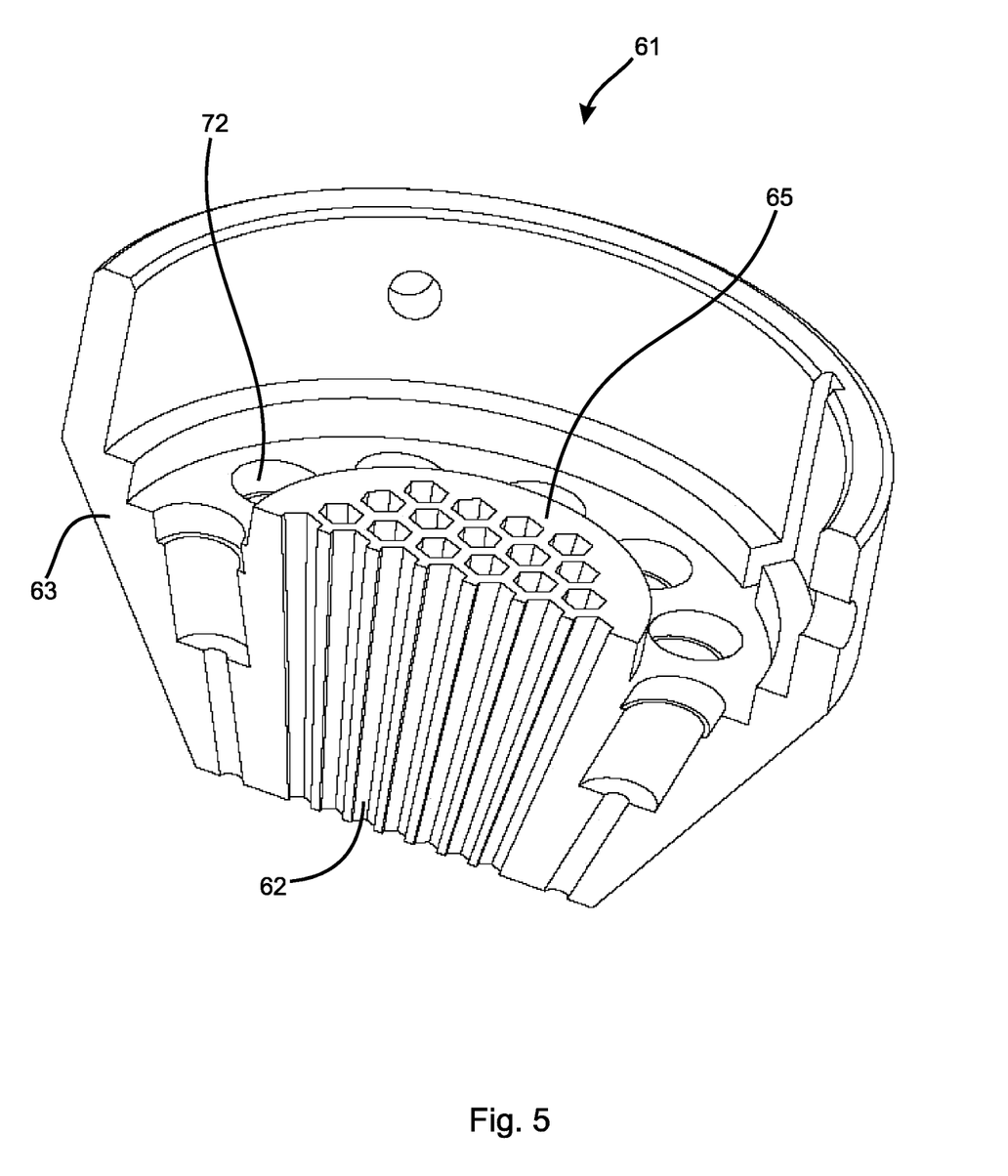
FIG. 5 depicts a cross-section through A-A of the collimator of FIG. 4A.

The collimator 61 is illustrated in more detail in FIG. 4A, FIG. 4B, FIG. 4C, FIG. 4D and FIG. 5. The collimator 61 comprises a generally frusto-conical block 63 of stainless steel having a gamma ray input face 64 and a gamma ray output face 65. Extending between the input and output faces 64, 65 is a close-packed hexagonal array of thirty-seven converging channels 62 (only one labeled) converging toward the input face 64. Each of the channels 62 has a tapered hexagonal cross-section having a greater area at the output face 65 than at the input face 64. The channels 62 taper at an angle of about 2° with respect to longitudinal axes through the channels 62, as best seen in FIG. 5. The channels 62 are configured to collect gamma rays substantially only from a focal point P about 35 mm below the input face 64 in an x-y plane, and to transmit gamma rays from the output face 65 to a scintillator of the conventional crystal-based gamma detector. The collimator 61 is adequately thick to prevent penetration of stray gamma rays, and has thin septa between the channels 62 to increase gamma ray collection efficiency. The 61 collimator provides high sensitivity and spatial resolution, facilitating real-time localization of radioactive regions. Although a frusto-conical block is illustrated, any shape of block may be used provided the block is of sufficient size to contain the channels.

In addition to being designed for gamma imaging, the collimator may be further configured with visible light imaging/localizing capability (e.g. an optical alignment system). An optical light source may be used in conjunction with the convergent collimator to project light onto a body of a patient, thereby providing visual feedback to provide an estimate of the position of the focal point relative to a surface of the patient's body. To this end, one or a plurality of visible light sources (e.g. high intensity LED lights) may be mounted on the collimator, preferably on the periphery, and focused on the same focal point to which the channels are focused. An optical imaging camera may be mounted on the gamma probe to measure the size of the projected light and to calculate an estimate for the relative position of the focal point to the surface.

When the gamma probe is being used to resolve a location of the gamma ray source, the channels provide highly resolved gamma ray localization in the x-y plane, but spatial resolution of the gamma ray source along a vertical (z-axis) is not as well resolved, due to the length of the channels. Therefore, once the gamma probe is positioned properly to localize the gamma ray source in the x-y plane, there still remains considerable uncertainty as to whether the gamma probe is correctly located along the z-axis, and therefore there is the same uncertainty as to the location of the gamma ray source along the z-axis. The visible light imaging/localizing capability further helps localize the gamma ray source along the z-axis because the visible light will only be in focus when the gamma probe is correctly located along the z-axis. When used in a combined gamma and ultrasound intraoperative imaging system, the gamma probe therefore also provides a third imaging modality, i.e. a visible light imaging modality, which provides visual co-localization for more accurate spatial resolution along the vertical axis (z-axis).

In one embodiment, an optical alignment system may comprise a plurality, for example twelve, high-intensity LED lights 70 (only one labeled) mounted annularly around a periphery of the array of channels 62 in the collimator 61, preferably outside of the sensitive region of the scintillator crystal, as shown in FIG. 4A, FIG. 4B, FIG. 4C, FIG. 4D and FIG. 5. The LED lights 70 are concentric with and aligned parallel to the channels 62 in the collimator 61, and are therefore co-aligned with the focal point P of the collimator 61 providing visual co-localization of a sensitive region of interest at the focal point P as seen in FIG. 4D. The LED lights 70 are mounted in LED mounts 72 (only one labeled) and shine through LED ports 71 (only one labeled) in the input face 64 of the collimator 61. The LED lights 70 may be any desired color, for example red, blue, green, yellow and the like, to provide good contrast with the sensitive region of interest to aid in visually detecting the location of the visible light. With the LED lights 70 forming a ring around the channels 62 in the collimator 61, a brightly colored light spot is formed at the same location as the gamma probe's sensitive region when the gamma probe 60 is being held in the correct location along the z-axis. In this way, an operator may be able to visually determine whether the gamma probe 60 is being held at a correct distance along the z-axis, and will be able to more clearly determine the location of the gamma source in all three dimensions when the gamma probe 60 detects gamma rays. Thus, the optical alignment system further facilitates real-time interrogation.

The optical alignment system provided an intense light spot that was geometrically co-aligned with the sensitive region of the gamma probe. This localizer light (created by the convergence of 12 ultra-bright LEDs) appeared similar to a laser pointer and was highly visible under normal lighting conditions, providing real-time localization of the interrogation volume of the gamma probe. An added benefit of the optical alignment system was the fact that it provided a clear indication of the depth of the focal spot, with respect to the collimator face. This was due to the fact that the LED sources only converged at one distance from the face (i.e. 35 mm in the embodiment described), and became quite dim when the probe was positioned either closer or farther away. The combined signal from the 12 ultra-bright LEDs was sufficient to allow operators to visualize the location of the sensitive region of the gamma probe, in x, y and z directions, which can provide valuable real-time feedback regarding the location of the sensitive volume of the probe.

To fabricate the collimator 61 in 3D, a computer-aided design software (TurboCad™) was used to design the configuration. For comparison, a similar collimator was designed and fabricated having cylindrical channels instead of tapered hexagonal channels. Collimator assemblies were fabricated in solid metal, using selective-laser melting (SLM). Three-dimensional design parameters were exported in stereolithographic file format (STL) and imported into custom software to generate build files for a commercial SLM machine (AM125, Renishaw plc). Components were fabricated in stainless-steel alloy (316L), using 30 µm layers. The AM125 uses a 200 W ytterbium fibre laser (1 µm wavelength) with a nominal focal spot size of 35 µm to fuse metal powder into fully dense metal. The selective-laser melting process took place in an inert argon atmosphere, to prevent oxygen contamination during the building process. After fabrication, collimators were inspected for dimensional accuracy and build quality. The measured thickness of septa between channels was typically less than about 250 µm, for example 25-250 µm, demonstrating that thin septa are possible with the SLM fabrication process. Adequate septal attenuation in the SLM-fabricated collimators may be ensured by employing long path-length channels through the collimator (e.g. about 20 mm) and relatively thick walls (e.g. about 0.2 to 0.9 mm thick). FIG. 5 illustrates the long path-length channels 62 that are possible using selective-laser melting in metal. This approach works well at 59.5 keV, but may provide lower spatial resolution at higher energies (for example the 140 keV gamma ray from $^{99m}$Tc).

3D computer-aided design and additive manufacturing made it possible to design and fabricate collimators efficiently and cost-effectively. The entire cycle from design to experimental testing required only a few days, facilitating rapid iteration and improvement of design concepts. The capabilities of additive manufacturing with selective-laser melting allow for very complex designs (such as long, tapered hexagonal channels) that would not be possible by conventional machining or casting.

The gamma probe 60 with focused collimator 61 was tested for sensitivity and spatial resolution, using a low-intensity sealed gamma source. A 0.9 µCi $^{241}$Am source retrieved from an expired smoke detector was employed. The $^{241}$Am is typically employed as an alpha source, but it also emits a gamma ray at 59.5 keV, making it useful for laboratory assessment of gamma detectors. The gamma ray source 66 was a 2 mm diameter button of $AmO_2$, as shown in FIG. 4D. The gamma ray source 66 was mounted on the precision x-y stage 67 (UTM50, Newport) controlled by a micro-stepping driver (ESP301, Newport). The gamma ray source 66 was held securely in a mounting plate 69, which allowed the gamma ray source 66 to be traversed at a fixed distance (35 mm) beneath the input face 64 of the collimator 61, as shown in FIG. 4D. To assess spatial resolution in terms of line-spread profile, the gamma ray source 66 was translated from −25 mm to +25 mm past the collimator focal spot, in 0.5 mm increments. FIG. 4C shows the stage 67 at the origin, with the LED alignment spot directly over the $^{241}$Am source 66. Count rates were recorded for 100 s at each location, and background count rates (typically 350 counts per minute (CPM)) were recorded with the $^{241}$Am source removed 66 from the test system. This test of spatial resolution was performed for each of the collimator designs (i.e. cylindrical or tapered hexagonal channels) and also for the case where no collimator was present. Data was fit to a Gaussian function using non-linear regression (Prism, Graphpad Inc.) Each collimator design was characterized by the full-width at half-maximum (FWHM).

Figure 6A:
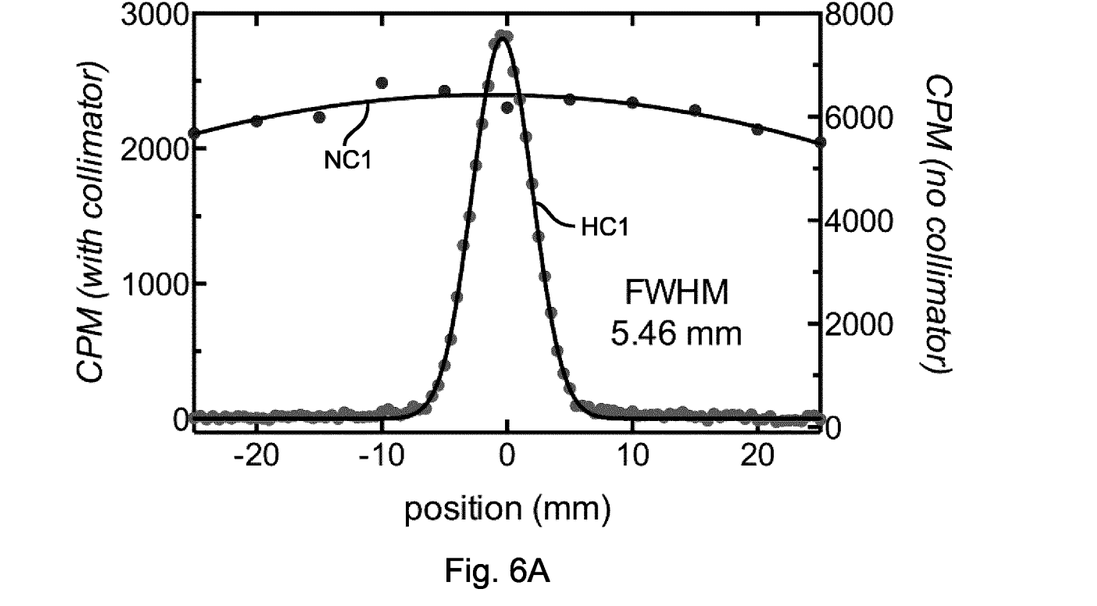
FIG. 6A depicts a graph of counts per minute (CPM) vs. position (mm) showing experimental results from a first test of sensitivity and spatial resolution using the collimator of FIG. 4A (curve HC1) compared with no collimator (curve NC1).

FIG. 6A depicts a graph of counts per minute (CPM) vs. position (mm) showing experimental results from a first test of sensitivity and spatial resolution using the collimator 61 (curve HC1) compared with no collimator (curve NC1). Spatial resolution in the x-y plane of about 5.5 mm (FWHM) and count rates of about 3000 CPM µCi$^{-1}$ were observed with the collimator 61. Almost no spatial resolution was obtained with no collimator, which showed essentially constant count rate at all source positions. Tumor sizes for surgery or biopsy typically have diameters of about 3-5 mm, therefore the spatial resolution provided by the collimator 61 is suitable for real-time imaging of the tumor. Further, efficiency of the gamma probe 60 with the collimator 61 was still very good.

Figure 6B:
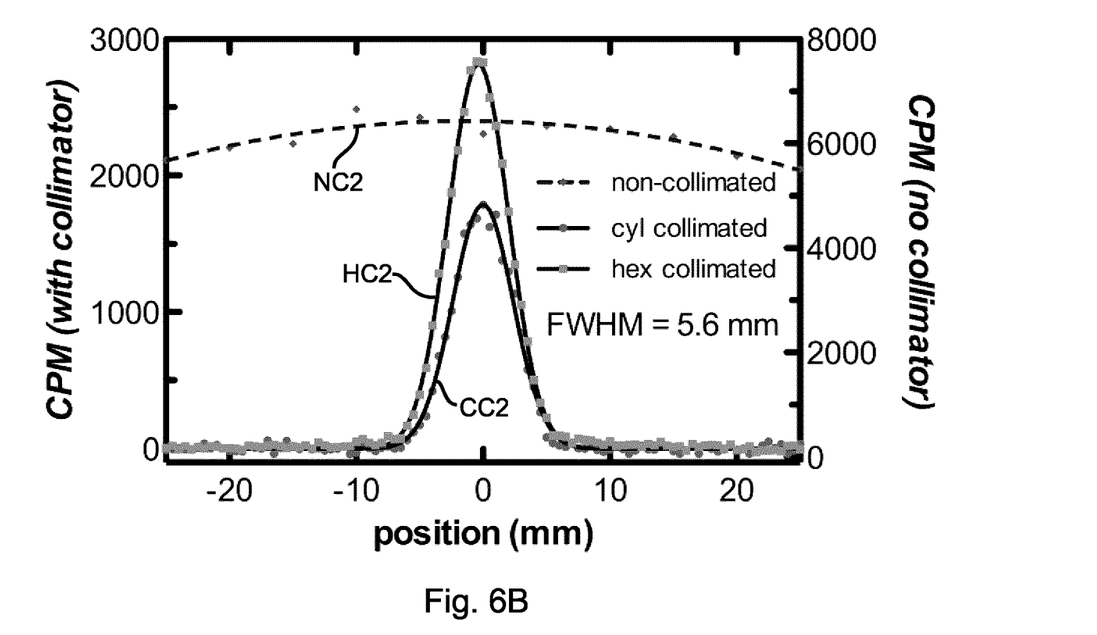
FIG. 6B depicts a graph of counts per minute (CPM) vs. position (mm) showing experimental results from a second test of sensitivity and spatial resolution using the collimator of FIG. 4A (curve HC2), using a collimator like the collimator of FIG. 4A except that the channels are cylindrical rather than hexagonal (curve CC2), and using no collimator (curve NC2).

FIG. 6B depicts a graph of counts per minute (CPM) vs. position (mm) showing experimental results from a second test of sensitivity and spatial resolution using the collimator 61 (curve HC2), using a collimator like the collimator 61 except that the channels are cylindrical rather than hexagonal (curve CC2) and using no collimator (curve NC2). With no collimator, the gamma detector demonstrated limited spatial resolution, with essentially constant count rate at all source positions. Both the cylindrical and hexagonal collimator designs showed good spatial resolution, with FWHM values of 5.58 mm and 5.60 mm, respectively. However, the geometric efficiency of the hexagonal close-packed collimator 61 was 1.5 times greater than the design with cylindrical channels, due to the significant increase in acceptance area achieved with the tapered hexagonal channel design. Compared to the observed peak count rate without a collimator (6425 CPM), both of the other collimators provided good geometric efficiency; 28.6% (1840 CPM) and 43.8% (2815 CPM) for the cylindrical and hexagonal designs, respectively. However, the hexagonal close-packed collimator 61 exhibited significantly superior geometric efficiency to the cylindrical design, providing a 50% increase in sensitivity over the cylindrical design.

It is apparent from FIG. 6A and FIG. 6B that the gamma probe 60 can achieve a spatial resolution in the x-y plane of less than 6 mm while being able to detect a radiation source emitting as little as 0.9 µCi of gamma rays. Typical tumors on which intraoperative surgical procedures are conducted have sizes in a range of about 3-6 mm and are labeled with radiolabels emitting gamma rays in a range of about 10-15 µCi. Therefore, the gamma probe 60 is well suited for such intraoperative surgical procedures.

In another embodiment, a collimator may comprise multiple convergent collimators with multiple focal zones, where each focal zone delivers photons to independent photon detectors (e.g. scintillators). The collimator may have multiple focal points and multiple photon detectors (e.g. scintillators) can be used to detect the gamma radiation received from each section of the collimator corresponding to a specific focal point. The detected gamma values from each of the focal points can be used to identify the direction towards a gamma ray source (hot spot) through an audio or visual feedback to a user. The focal points of the collimator may be designed to provide a matrix coverage of a plane of interest. In one aspect, the collimator may have two sections that both have the same focal point. One or two photon detectors can be used to obtain a stereo measurement of the gamma values coming from the same focal point and to allow for an accurate estimation of the depth of the source of the gamma rays.

Figure 7A:
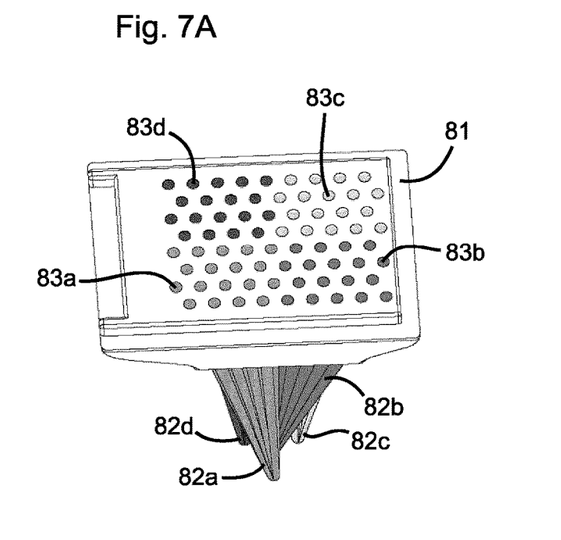
FIG. 7A and FIG. 7B depict schematic diagrams of another embodiment of a convergent collimator, the collimator having four focal zones within a single plane, each zone delivering photons to independent photon detectors.
Figure 7B:
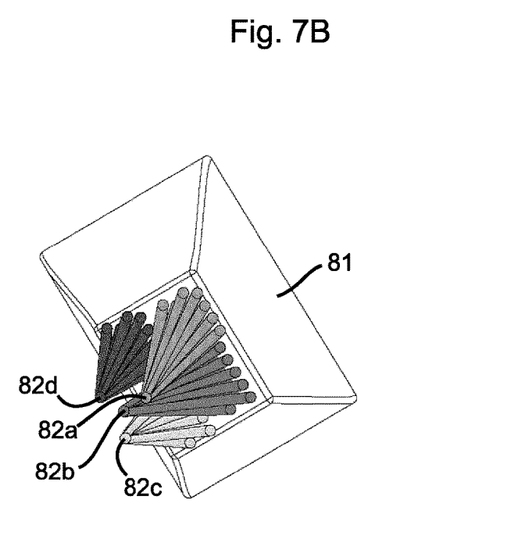

One example is shown in FIG. 7A and FIG. 7B, in which a convergent collimator 81 may comprise four focal zones 82a, 82b, 82c, 82d within a single plane, each zone delivering photons to independent photon detectors through independent arrays of channels 83a, 83b, 83c, 83d, respectively, in the collimator 81. With the configuration shown in FIG. 7A and FIG. 7B, ratiometric comparison of signals from the different focal zones may be used to triangulate the gamma ray source in the x-y plane to provide greater spatial resolution of the gamma ray source in the x-y plane.

Figure 7C:
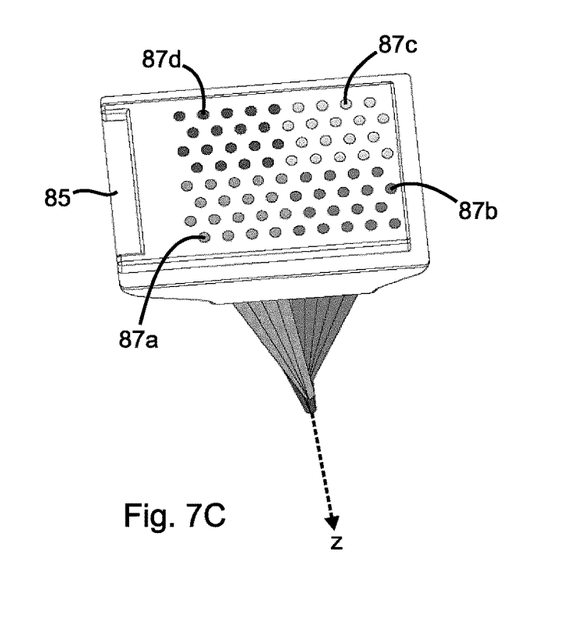
FIG. 7C and FIG. 7D depict schematic diagrams of another embodiment of a convergent collimator, the collimator having four focal zones specified at different points along a z-axis, each zone delivering photons to independent photon detectors.
Figure 7D:
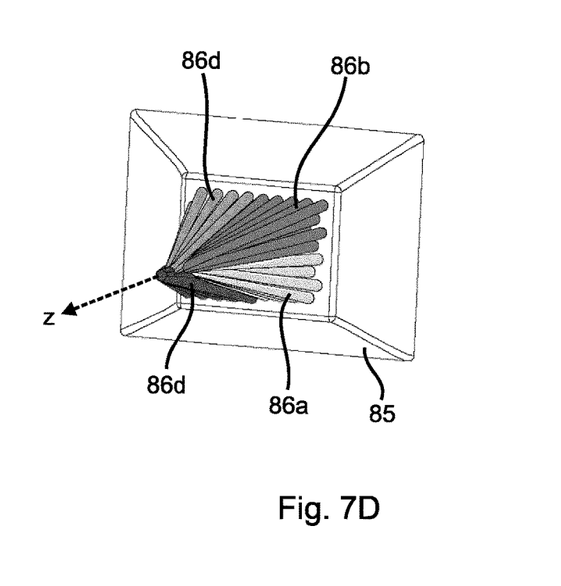

Another example is shown in FIG. 7C and FIG. 7D, in which a convergent collimator 85 has four focal zones 86a, 86b, 86c, 86d specified at different points along a z-axis, each zone delivering photons to independent photon detectors through independent arrays of channels 87a, 87b, 87c, 87d, respectively, in the collimator 85. With the configuration shown in FIG. 7C and FIG. 7D, ratiometric comparison of signals from the four different focal zones at the same point in the x-y plane but at different depths along the z-axis may be used to obtain depth information of the gamma ray source.

Figure 8:
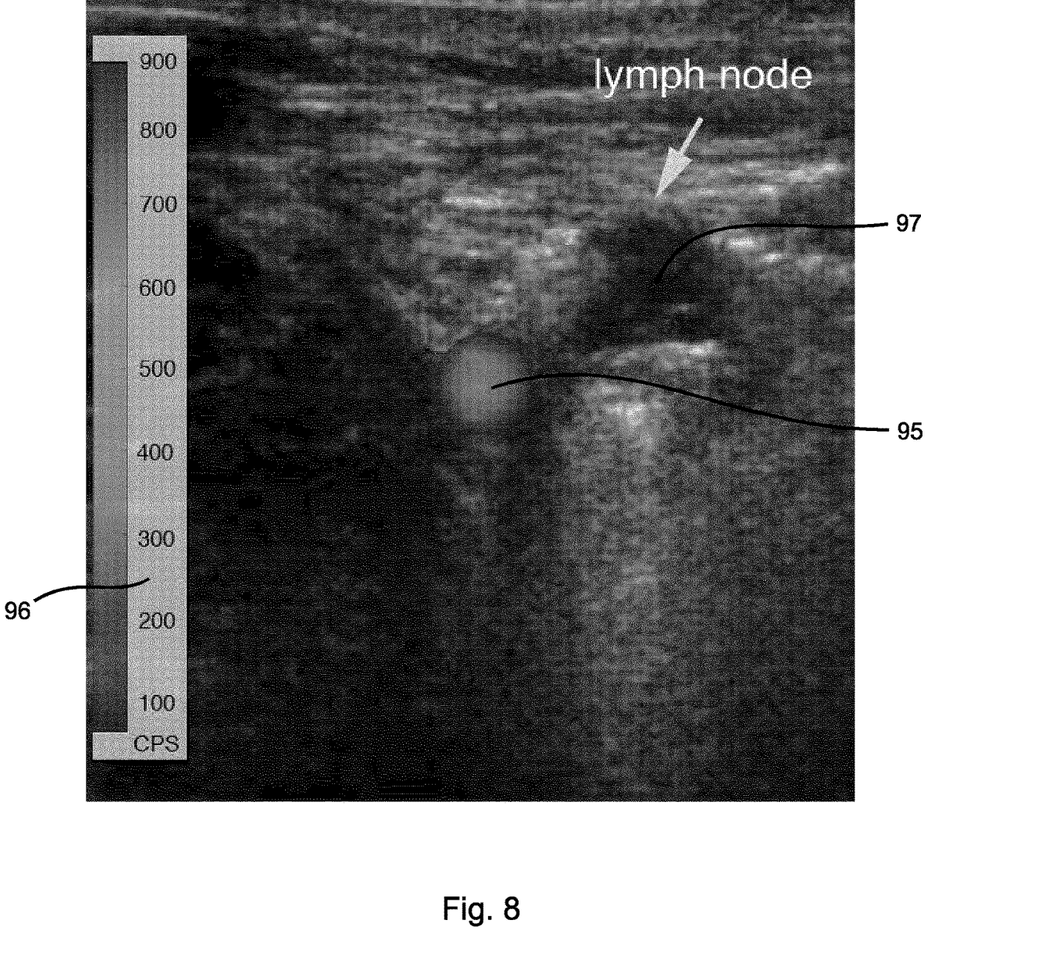
FIG. 8 depicts a simulated display image showing real-time integration of an ultrasound image and gamma activity collected using a combined gamma and ultrasound intraoperative imaging system of the present invention.

FIG. 8 depicts a simulated display image showing real-time integration of an ultrasound image and gamma activity collected using a combined gamma and ultrasound intraoperative imaging system, such as the intraoperative imaging system 1 shown in FIG. 1. The focal point of the gamma probe intersects the detection plane of the ultrasound probe at a co-registered region of interest 95, seen close to a lymph node 97 in the ultrasound image shown in FIG. 8. Activity within the co-registered region of interest 95 can be presented as a color overlay or a gray scale, scaled to be consistent with known Full Width Half Maximum (FWHM). A calibrated color or gray scale bar 96 indicates activity in Bq. Thus, by measuring the relative position of the gamma probe with respect to the ultrasound probe and by utilizing a collimator with known focal point, the detected values of gamma radiation can be graphically represented to the user. The estimate of spatial positioning of the source of the gamma rays, alongside graphical representation of the amount of activity, can be overlaid on the acquired ultrasound images and presented in real-time.

The ultrasound probe may comprise a 2D ultrasound transducer that can be tracked spatially and swept across the tissue while the images are recorded with a tag of the positions from which the images were acquired. The images can be used to then reconstruct a 3D image of the tissue. The ultrasound transducer may instead be a 3D ultrasound imaging system that utilizes multiple arrays of ultrasound transducers.

The relative position of the two imaging modalities may be adjusted. Relative position adjustment may be accomplished manually or by using an actuator. The relative position of the two imaging probes may be adjusted so that the focal point of the gamma probe is maintained within the imaging field of view of the ultrasound probe.

The combined gamma and ultrasound intraoperative imaging system 1 depicted in FIG. 1 is a hand-held system in which the gamma probe 10 is mechanically linked to the ultrasound probe 30. However, the gamma probe and ultrasound probe do not need to be mechanically linked. Instead, the gamma probe and ultrasound probe may be tracked independently.

Tracking of the gamma probe, ultrasound probe or both may be accomplished using a tracking system, for example an optical, electromagnetic or mechanical position tracking system. The tracked position of the gamma probe can be registered with preoperative 3D volumetric images obtained from the patient (e.g. CT or MRI). Anatomical landmarks on the patient can be pointed to with the gamma probe as the gamma probe is tracked. The points can be identified on preoperative images and used to register the gamma probe position relative to the 3D volumetric images.

Figure 9:
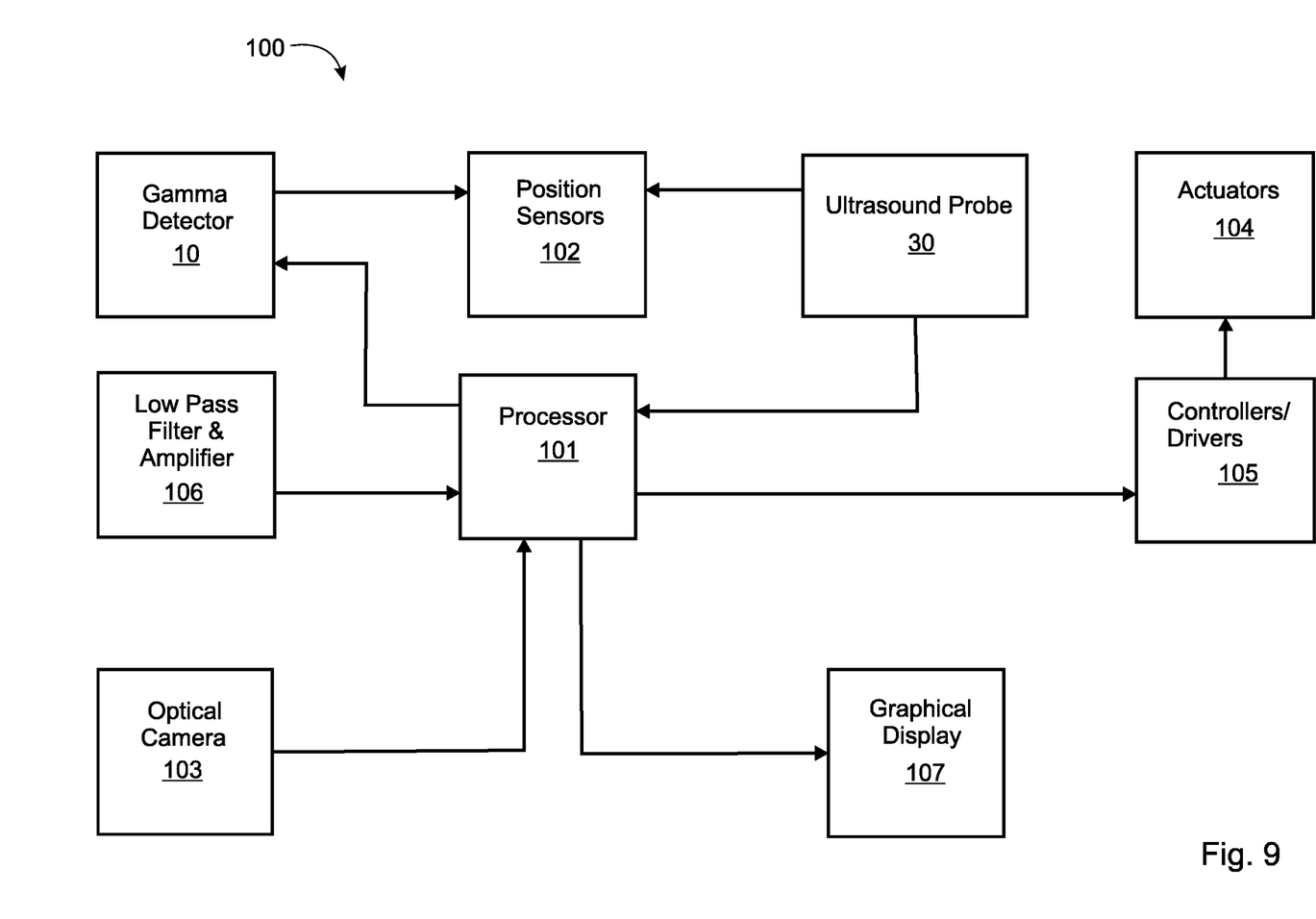
FIG. 9 depicts a block diagram illustrating an embodiment of a system implementation for a combined gamma and ultrasound intraoperative imaging system of the present invention.

FIG. 9 depicts a block diagram illustrating an embodiment of a system implementation for a combined gamma and ultrasound intraoperative imaging system. The block diagram shows interactions of various system components for a combined gamma and ultrasound intraoperative imaging system 100 including the gamma probe 10 and the ultrasound probe 30 integrated with various other functional components. A central processor 101 captures information from an ultrasound probe 30, position sensors 102, an optical camera 103 and the gamma probe 10. Signals from the gamma probe 10 are passed through a low pass filer & amplifier 106 before being processed by the processor 101. The processor 101 uses the captured information to determine motion of an actuator 104 required to maintain the focal point of the gamma probe 10 in the imaging plane of the ultrasound probe 30. Based on the determined motion, the processor 101 signals one or more controllers/drivers 105 to actuate one or more actuators 104 in the required manner. Information received by the processor 101 from the gamma probe 10 and the ultrasound probe 30 are overlaid and presented to a user on an output device, for example a graphical display 107.

Figure 10A:
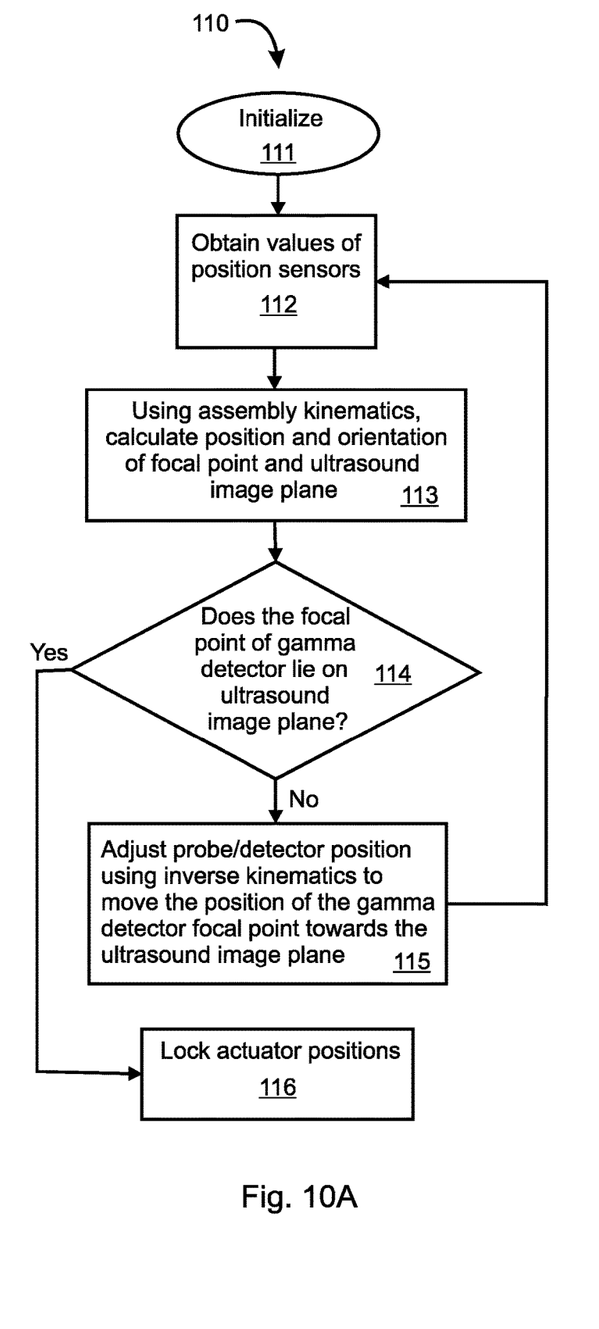
FIG. 10A depicts a flowchart of one embodiment of an algorithm that may be run on a processor in the system implementation of FIG. 9.

FIG. 10A depicts a flowchart illustrating an embodiment of an algorithm 110, which may be used for automatic adjustment of the relative position of the ultrasound probe 30 with respect to the gamma probe 10 of the system 100 depicted in FIG. 9. The algorithm 110 may be embodied in computer software programmed into the processor 100. The algorithm 110 comprises:

111—initializing the system 100;
    112—obtaining sensor values from the position sensors 102;
    113—using sensor values and assembly kinematics to calculate position and orientation of the gamma probe focal point and the ultrasound image plane;
    114—determining whether the focal point of the gamma probe 10 lies on the image plane of the ultrasound probe 30;
    If no, go to 115. If yes, go to 116.
    115—adjusting position of the gamma probe 10 and/or the ultrasound probe 30 using inverse kinematics to move the gamma probe focal point towards the ultrasound image plane;
    116—locking positions of the actuators 104.

Figure 10B:
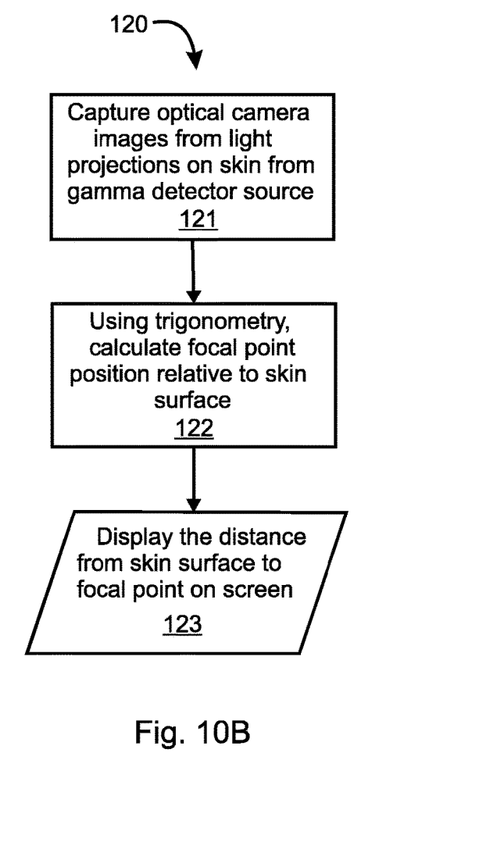
FIG. 10B depicts a flowchart of one embodiment of an algorithm to estimate position of a focal point of a gamma probe with respect to an image plane of an ultrasound probe in the system implementation of FIG. 9.

FIG. 10B depicts a flowchart of an algorithm 120 to execute step 113 in FIG. 10A. The algorithm 120 may be embodied as computer software programmed into the processor 101, and automatically estimates the position and orientation of the focal point of the gamma probe 10 with respect to the image plane of the ultrasound probe 30. The algorithm 120 comprises:

121—using the optical camera 103, capturing images of visible light projections on a patient's exposed skin surface, the visible light projections generated by the optical alignment system associated with the gamma probe 10;
    122—using trigonometry, calculate focal point position relative to the skin surface to determine a distance from the skin surface to the focal point;
    123—displaying the distance from the skin surface to the focal point on the graphical display 107.

The algorithms 110 and 120 may be used to maintain the focal point of the gamma probe 10 within the field of view of the second imaging modality, e.g. the ultrasound probe 30.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. An intraoperative imaging system comprising a gamma probe configured to detect gamma radiation emitted from a source of gamma radiation in a radiolabeled tissue and an ultrasound probe configured to acquire an ultrasound image of the radiolabeled tissue, the gamma probe and ultrasound probe linked to provide co-registration of the gamma radiation with the ultrasound image, the gamma probe comprising a converging collimator for gamma rays, the collimator comprising:

a metal block having a gamma ray input face and a gamma ray output face;
    a plurality of channels in the metal block converging from the output face toward the input face, each channel extending between the input face and the output face, each channel having a first opening at the input face and a second opening at the output face, wherein the first opening has a smaller cross-sectional area than a cross-sectional area of the second opening and each channel tapers inwardly from the output face to the input face; and,     a focal point outside the collimator and distant from the input face,
    the system further comprising an optical alignment sub-system having a focal point, the optical alignment sub-system configured to focus visible light to converge at the focal point of the collimator thereby providing a visual indication of a position of the focal point of the collimator, whereby the source of gamma radiation, the focal point of the collimator and the focal point of the optical alignment sub-system are all co-located in space in the radiolabeled tissue,
    wherein the optical alignment sub-system comprises a plurality of visible light sources mounted on the collimator and disposed annularly around a periphery of the plurality of channels, the plurality of visible light sources aligned and directed to focus the visible light at the focal point of the collimator.

2. The system of claim 1, wherein the visible light sources are high-intensity light emitting diodes (LEDs).

3. The system of claim 1, wherein the optical alignment sub-system further comprises an optical imaging camera configured to acquire images of the visible light focused at the focal point of the collimator.

4. The system of claim 1, further comprising one or more actuators, and relative position of the gamma probe and ultrasound probe is adjusted by the one or more actuators to maintain the focal point of the collimator in an imaging field of the ultrasound probe.

5. The system of claim 1, wherein the relative position of the gamma probe and ultrasound probe is tracked to provide relative spatial tracking information and the relative spatial tracking information provides for the co-registration of the image acquired by the ultrasound probe with gamma ray counts acquired by the gamma probe.

6. The system of claim 5, wherein the gamma probe is mechanically linked to the ultrasound probe, the probes are able to move relative to each other with confined kinematics, and the relative spatial tracking information is determined using the confined kinematics and one or more position sensors.

7. The system of claim 5, wherein the gamma probe is not mechanically linked to the ultrasound probe, and the intraoperative imaging system further comprises a tracking sub-system that tracks positions of the gamma probe and the ultrasound probe independently.

8. The system of claim 1, wherein each channel of the collimator tapers inwardly at a taper angle in a range of 0.8° to 6° with respect to a longitudinal axis of the channel.

9. The system of claim 8, wherein the taper angle is in a range of 1° to 3°.

10. The system of claim 1, wherein the channels are separated in the metal block by thin septa of metal having thicknesses of less than 250 µm.

11. The system of claim 1, wherein the plurality of channels is sectioned into two or more sections, each section having a different focal point.

12. The system of claim 1, wherein the plurality of channels is configured in a close-packed hexagonal array and each channel has a hexagonal cross-section.

13. A method of imaging a radiolabeled tissue in a body of a patient in real-time, the method comprising: acquiring an ultrasound image and a corresponding gamma ray count at a location in the body with an intraoperative imaging system as defined in claim 1; and, displaying in real-time the ultrasound image with the corresponding gamma ray counts co-registered thereon to determine whether the radiolabeled tissue is at the location.

14. The system of claim 1, wherein the metal block comprises tungsten.

\* \* \* \* \*